US007078387B1

(12) United States Patent
Leiden et al.

(10) Patent No.: US 7,078,387 B1
(45) Date of Patent: Jul. 18, 2006

(54) EFFICIENT AND STABLE *IN VIVO* GENE TRANSFER TO CARDIOMYOCYTES USING RECOMBINANT ADENO-ASSOCIATED VIRUS VECTORS

(75) Inventors: Jeffrey M. Leiden, Weston, MA (US); Eric Svensson, Chicago, IL (US)

(73) Assignee: Arch Development Corp., Chicago, IL (US)

(*) Notice: Subject to any disclaimer, the term of this patent is extended or adjusted under 35 U.S.C. 154(b) by 143 days.

(21) Appl. No.: 09/473,830

(22) Filed: Dec. 28, 1999

Related U.S. Application Data

(60) Provisional application No. 60/113,923, filed on Dec. 28, 1998.

(51) Int. Cl.
*A01N 43/04* (2006.01)
*A01N 63/00* (2006.01)
*C12N 63/00* (2006.01)
*C12N 15/63* (2006.01)
*C07H 21/04* (2006.01)

(52) U.S. Cl. .................. 514/44; 424/93.21; 435/320.1; 435/455; 536/23.1; 536/23.5; 536/24.1

(58) Field of Classification Search .................. 514/44; 435/320.1, 325, 455; 424/93.1, 93.21; 536/24.1, 536/23.1, 23.5
See application file for complete search history.

(56) References Cited

U.S. PATENT DOCUMENTS

| 5,661,133 A | 8/1997 | Leiden et al. |
| 5,705,388 A | 1/1998 | Couture et al. |
| 5,792,453 A | 8/1998 | Hammond et al. |
| 5,846,528 A | 12/1998 | Podsakoff et al. |
| 5,858,351 A * | 1/1999 | Podsakoff et al. ......... 424/93.2 |
| 5,661,133 A | 6/1999 | Leiden et al. |
| 6,100,242 A | 8/2000 | Hammond et al. |

FOREIGN PATENT DOCUMENTS

| WO | WO 97/12050 | 4/1997 |
| WO | WO 97/26337 | 7/1997 |
| WO | WO 97/32990 | 9/1997 |
| WO | WO 98/46728 | 10/1998 |
| WO | WO 99/07833 | 2/1999 |

OTHER PUBLICATIONS

Crystal, R. G. Transfer of genes to humans: early lessons and obstacles to success. Science, vol. 270, pp. 404-410. 1995.*
Anderson, W. F. Human gene therapy. Nature, vol. 392. pp. 25-30. 1998.*
Verma et al., Gene therapy-promises,problems and propspects, Sep. 18, 1997, Nature, vol. 389, pp. 239-242.*
Eck et al., Gene Based Therapy, 1996, Goodman & Gilman's The Pharmacological of Basis of Therapeutics, Chaphter 5, Ninth Edition, pp. 77-101.*
Alexander, Ian, et al., "Transfer of Contaminants in Adeno-Associated Virus Vector Stocks Can Mimic Transduction and Lead to Artifactual Results," Hum. Gene Ther. 8: 1911-1920 (1997).
Gnatenko, Dmitri, et al. "Characterization of Recombinant Adeno-Associated Virus-2 as a Vehicle for Gene Delivery and Expression into Vascular Cells," J. Invest. Med. 45: 87-98 (1997).
Kaplitt, Michael G., et al., "Long-Term Gene Transfer in Porcine Myocardium After Coronary Infusion of an Adeno-Associated Virus Vector," Ann. Thorac. Surg. 62: 1669-1676 (1996).
Kessler, Paul D., et al., "Sodium Butyrate Greatly Enhances the Efficiency of Viral Transduction in Adult Ventricular Cardiomyocytes by Adeno-associated Viral Vectors," Circulation, Supp. 1 92: I-296, Abstract 1408 (1995).
Maeda, Yoshikazu, et al., "Efficient Gene Transfer into Cardiac Myocytes Using Adeno-Associated Virus (AAV) Vectors,",J. Mol. Cell. Cardiol. 30: 1341-1348 (1998).
Phillips, Ian M., et al., "Prolonged Reduction of High Blood Pressure With an In Vivo. Nonpathogenic, Adeno-Associated Viral Vector Delivery of $AT_1$-R mRNA Antisense," Hypertension 29: 374-380 (1997).
Ping, P., et al. "Altered β-Adrenergic Receptor Signaling In Heart Failure, In Vivo Gene Transfer Via Adeno and Adeno-Associated Virus," Microcirculation, 3: 225-228 (1996).
Dourtis, A. P., et al., "Cardiac Gene Therapy with Adeno-Associated Virus as a Means of Achieving Graft-specific Immunosuppression," Mod. Pathol. 8: 33A, Abstract 178 (1995).
Rolling, Fabienne, et al., "AAV as a Viral Vector for Human Gene Therapy," Mol., Biotechnol. 3: 9-15 (1995).
Kessler, et al., "Gene Delivery To Skeletal Muscle Results In Sustained Expression and Systemic Delivery of A Therapeutic Protein," Proc. Natl. Acad. Sci. USA 93: 14087-97 (1996).

(Continued)

Primary Examiner—Shin-Lin Chen
(74) Attorney, Agent, or Firm—Fulbright & Jaworski, LLP

(57) ABSTRACT

This invention relates to the use of recombinant adeno-associated virus (rAAV) vectors to transduce cardiomyocytes in vivo by infusing the rAAV into a coronary artery or coronary sinus. rAAV infection is not associated with detectable myocardial inflammation or myocyte necrosis. Thus, rAAV is a useful vector for the stable expression of therapeutic genes in the myocardium and can be used to deliver genes for inducing angiogenesis, inhibiting angiogenesis, stimulating cell proliferation, inhibiting cell proliferation and/or treating or ameliorating other cardiovascular conditions.

15 Claims, 2 Drawing Sheets

OTHER PUBLICATIONS

Connolly, Daniel T et al., "Vascular Permeability Factor: A Unique Regulator of Blood Vessel Function," J. Cell. Biochem. 47:219-223 (1991).

Conrad, C.K. et al., "Safety of Single-Dose Administration of an Adeno-Associated Virus (AAV)-CFTR Vector in the Primate Lung," Gene Ther. 3:658-668 (1996).

Crumley, Gregg et al., "The Gene for Human Acidic Fibroblast Growth Factor Encodes Two Upstream Exons Alternatively Spliced to the First Coding Exon," Biochem. Biophys. Res. Commun. 171:7-13 (1990).

During, M.J. et al. "In Vivo Expression of Therapeutic Human Genes for Dopamine Production in the Caudates of MPTP-Treated Monkeys using an AAV vector," Gene Ther. 5:820-827 (1998).

Flotte, Terence R. et al., "Stable In Vivo Expression of the Cystic Fibrosis Transmembrane Conductance Regulator with an Adeno-Associated Virus Vector," Proc. Natl. Acad. Sci. USA 90:10613-10617 (1993).

Flotte, Terence et al., "A Phase I Study of an Adeno-Associated Virus-CFTR Gene Vector in Adult CF Patients with Mild Lung Disease," Hum. Gene Ther. 7:1145-1159 (1996).

Folkman, Judah et al., "Angiogenic Factors," Science 235:442-447 (1987).

Kotin, Robert M., "Prospects for the Use of Adeno-Associated Virus as a Vector for Human Gene Therapy," Hum. Gene Ther. 5:793-801 (1994).

Kourtis, A.P. et al., "Cardiac Gene Therapy with Adeno-Associated Virus as a Means of Achieving Graft-Specific Immunosuppression," Modern Pathology 8:Abstract No. 178 (1995).

Kurachi, Kotoku et al., "Sequence of the cDNA and Gene for Angiogenin, a Human Angiogenesis Factor," Biochemistry 24:5494-5499 (1985).

Kurokawa, Tsutomu et al., "Cloning and Expression of cDNA Encoding Human Basic Fibroblast Growth Factor," FEBS Lett. 213:189-194 (1987).

Lebkowski, Jane S. et al., "Adeno-Associated Virus: a Vector System for Efficient Introduction and Integration of DNA into a Variety of Mammalian Cell Types," Mol. Cell. Biol. 8:3988-3996 (1988).

Leung, David W. et al., "Vascular Endothelial Growth Factor is a Secreted Angiogenic Mitogen," Science 246:1306-1309 (1989).

Lynch, Carmel M. et al., "Adeno-Associated Virus Vectors for Vascular Gene Delivery," Circ. Res. 80:497-505 (1997).

Maeda, Yoshikazu et al., "Gene Transfer into Vascular Cells Using Adeno-Associated Virus (AAV) Vectors," Cardio. Res. 35:514-521 (1997).

Monahan, P.E. et al., "Direct Intramuscular Injection with Recombinant AAV Vectors Results in Sustained Expression in a Dog Model of Hemophilia," Gene Ther. 5:40-49 (1998).

Podsakoff, Greg et al., "Efficient Gene Transfer into Nondividing Cells by Adeno-Associated Virus-Based Vectors," J. Virol. 68:5656-5666 (1994).

Schaper, W., "Angiogenesis in the Adult Heart," Basic Res. Cardiol. 86(Supp. 2):51-56 (1991).

Snyder, Richard O., "Persistent and Therapeutic Concentrations of Human Factor IX in Mice After Hepatic Gene Transfer of Recombinant AAV Vectors," Nature Genet. 16:270-276 (1997).

Svensson, Eric C. et al., "Efficient and Stable Transduction of Cardiomyocytes After Intramyocardial Injection or Intracoronary Perfusion With Recombinant Adeno-Associated Virus Vectors," Circulation 99:201-205 (1999).

"Phase I Randomized Study of Adeno-Associated Virus-CFTR Vector in Patients with Cystic Fibrosis," www.clinicaltrials.gov/ct/gui/c/w1r/show/NCT00004533?order=1&JservSessionldzone_ct=xnrwsoycu1 (downloaded from website on Jun. 13, 2002).

* cited by examiner 2 weeks 4 weeks 8 weeks

EFFICIENT AND STABLE IN VIVO GENE TRANSFER TO CARDIOMYOCYTES USING RECOMBINANT ADENO-ASSOCIATED VIRUS VECTORS

This application is a continuation-in-part application of provisional application U.S. Ser. No. 60/113,923, filed Dec. 28, 1998, which is incorporated by reference herein in its entirety.

This work was supported in part by grants from the National Institutes of Health (DK-48997, AR-42895, and HL-54592) to Jeffrey M. Leiden.

FIELD OF THE INVENTION

The ability to stably and efficiently program recombinant gene expression in cardiomyocytes facilitates gene therapy approaches for a variety of cardiovascular diseases and conditions. Accordingly, this invention relates to the use of recombinant adeno-associated virus (rAAV) vectors to transduce cardiomyocytes in vivo by infusing the rAAV into a coronary artery or coronary sinus. For example, coronary artery perfusion of mouse hearts with a rAAV encoding the LacZ gene produced efficient transduction of cardiomyocytes which was stable for at least 8 weeks. Moreover, rAAV infection is not associated with detectable myocardial inflammation or myocyte necrosis. Thus, rAAV is a useful vector for the stable expression of therapeutic genes in the myocardium and can be used to deliver genes for inducing angiogenesis, inhibiting angiogenesis, stimulating cell proliferation, inhibiting cell proliferation and/or treating or ameliorating other cardiovascular conditions.

BACKGROUND OF THE INVENTION

Myocardial gene therapy can be used for the treatment of a number of cardiovascular diseases, including ischemic cardiomyopathies, congestive heart failure, and malignant arrhythmias (Nabel (1995) Circulation 91:541–548). A useful vector for myocardial gene delivery will allow efficient and stable transduction of cardiomyocytes with a variety of transgenes after either direct intramyocardial injection or infusion into the coronary arteries or sinuses. For example, plasmid DNA vectors injected directly into the left ventricular myocardium have been expressed for ≧6 months by cardiomyocytes adjacent to the area of injection (Lin et al. (1990a) Circulation 82:2217–2221; Kass et al. (1993) Proc. Natl. Acad. Sci. USA 90:11498–11502; and Guzman et al. (1993) Circ. Res. 73: 1202–1207). However, the therapeutic usefulness of this approach has been limited by the low efficiency of cardiomyocyte transduction (0.1% to 1.0% of cardiomyocytes in the area of injection).

Both intramyocardial injection and intracoronary infusion of replication-defective adenovirus (RDAd) vectors have been used to efficiently transduce cardiomyocytes in rodents, rabbits, and pigs in vivo. However, the feasibility of adenovirus-mediated gene transfer has been limited by immune responses to viral and foreign transgene proteins, which cause significant myocardial inflammation, eliminate virus-transduced cells within 30 days of infection, and thereby result in transient recombinant gene expression in immunocompetent hosts (Guzman et al. (1993) Circ. Res.73: 1202–1207; French et al.(1994) Circulation 90:2414–2424; and Barr et al.(1994) Gene Ther. 1:51–58).

Recently, rAAV vectors have been shown to program efficient and stable recombinant gene expression in skeletal muscle and liver in both rodents and primates (Fisher et al.(1997) Nat. Med. 3:306–312; Kessler et al. (1996) Proc. Natl. Acad. Sci. USA 93:14082–14087; and Snyder et al. (1997) Nat. Genet. 16: 270–276) and in cardiac muscle directly injected with rAAV (U.S. Pat. No. 5,858,351 to Podsakoff et al.). However, since rAAV vectors used in gene therapy applications, unlike RDAd, do not encode viral proteins, the rAAV vectors have not been associated with immune responses to foreign transgene proteins.

While a previous report showed that rAAV can transduce cardiomyocytes in vivo, the efficiency of rAAV-mediated transgene expression in the heart was both low (about 0.2%) and localized (Kaplitt et al. (1996) Ann. Thorac. Surg. 62:1669–1676). In that study, pigs hearts were rapidly perfused with a low titer of rAAV (less than $10^4$ expressing units AAV per gram of body weight). Based on those results, infusing rAAV into the heart would have severely limited use as a vector for myocardial gene therapy. However, as demonstrated herein, this invention establishes that by infusing rAAV in much higher amounts proportional to body weight of the animal and for particular time periods, then rAAV provides unexpected efficient and stable gene transfer into the heart, opening up use of rAAV vectors to deliver therapeutically-effective molecules to cardiomyocytes in amounts useful for treating or ameliorating cardiac diseases or conditions.

SUMMARY OF THE INVENTION

The present invention is directed to a method of treating a cardiovascular condition by infusing an rAAV vector into a coronary artery or a coronary sinus for a time and in an amount sufficient to stably and efficiently transduce the cardiomyocytes perfused by the artery or sinus. The rAAV vector encodes at least one nucleic acid which is operably linked to a control region and which encodes a therapeutically-effective molecule. After infusion and transduction of the cardiomyocytes, the therapeutically-effective molecule is expressed in an amount effective to treat or ameliorate the cardiovascular condition.

Thus, this method provides a means of delivering AAV vectors in a stable and efficient manner. The vector can be infused by any convenient means and in conjunction with surgery or other cardiac procedure, if desired.

DETAILED DESCRIPTION OF THE INVENTION

Figure 1:
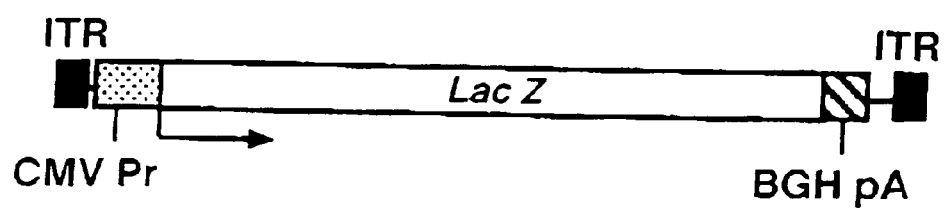
FIG. 1. Schematic of $AAV_{cMV\text{-}LacZ}$. ITR indicates inverted terminal repeats; BGH pA, bovine growth hormone polyadenylation signal; CMV Pr, CMV immediate-early promoter; LacZ, bacterial LacZ gene.

This invention relates to treating cardiovascular conditions using rAAV vectors. In accordance with the invention, an rAAV vector encoding a therapeutically effective molecule is infused into a coronary artery or a coronary sinus to deliver the vector to the heart in a manner which stably and efficiently transduces cardiomyocytes. It has unexpectedly been found that the ability to obtain stable and efficient transduction of cardiomyocytes by rAAV depends upon the duration of the infusion period and the amount of virus infused relative to body weight.

Moreover, rAAV displays significant advantages for myocardial gene transfer compared with plasmid DNA or adenovirus vectors. For example, rAAV, when delivered as described herein, allows efficient transduction of cardiomyocytes. Further, rAAV vectors program stable expression of foreign transgenes in immunocompetent hosts. The stability of transgene expression observed with rAAV even after expression of a foreign transgene protein likely reflects the fact that rAAV vectors, unlike their adenovirus counterparts, do not express any viral gene products and are therefore significantly less immunogenic. This lack of immunogenicity represents a major advantage of rAAV for myocardial gene transfer.

Hence, the invention is directed to a method of treating a cardiovascular condition which comprises infusing an rAAV vector into a coronary artery or sinus of an animal for a time and in an amount sufficient to stably and efficiently transduce cardiomyocytes perfused by the artery or sinus, wherein that vector encodes at least one nucleic acid, i.e., the transgene, encoding a therapeutically-effective molecule; and expressing the therapeutically-effective molecule in an amount effective to treat or ameliorate the cardiovascular condition. Further, the nucleic acid is operably linked to a control region, e.g., promoters, enhancers, termination signals and the like, to permit expression of the molecule. When more than one nucleic acid is present on the rAAV vector, each can be controlled separately by individual control regions or, any group of them, or all of them, can be controlled in an operon, i.e, with one control region driving expression of multiple genes on a single transcript.

rAAV vectors useful in the present invention can be any rAAV vector with one or more transgenes (or nucleic acids of interest) inserted therein in a manner allowing expression of the transgene under control of appropriate regulatory elements such as promoters, enhancers, transcription terminators and the like. rAAV vectors are well known in the art and can be prepared by standard methodology know to those of ordinary skill in the art. For example, U.S. Pat. No. 5,858,351 and the references cited therein describe a variety of rAAV vectors suitable for use in gene therapy as well as how to make and propagate those vectors (see, e.g., Kotin (1994) Human Gene Therapy 5:793–801 or Berns, "Parvoviridae and their Replication" in Fundamental Virology, 2nd Edition, (Fields & Knipe, eds.)).

A "transgene" or "nucleic acid of interest" or the "nucleic acid encoded in the rAAV vector" as used herein refers to any nucleotide sequence which encodes a therapeutically-effective molecule that can be used to treat a cardiovascular condition. Such transgenes may normally be foreign to the animal being treated or may be a gene normally found in that animal for which altered expression (e.g., temporal, spatial or amount of expression) is desired to achieve a particular therapeutic effect. The therapeutically-effective molecule encoded by the transgene is protein or an anti-sense RNA that imparts a benefit to the animal or subject undergoing treatment or amelioration of a cardiac condition or disease in accordance with this invention.

Proteins that can be administered to treat or ameliorate cardiovascular conditions are numerous and include, but are not limited to, molecules competent to induce angiogenesis, e.g., angiogenesis factors; anti-angiogenesis factors; proteins capable of inhibiting vascular smooth muscle cell proliferation; proteins useful for treating atherosclerosis; proteins useful for treating restenosis, proteins useful for stimulating cardiomyocyte activity; proteins capable of secretion from cardiomyocytes that exert their effect in the heart or capable of transport to other locales for treatment of a cardiovascular condition or disease; hormones, cytokines or growth factors useful for treating cardiac conditions or diseases; and proteins capable of stimulating vascular smooth muscle cell proliferation. Other genes encoding proteins useful in this invention include ion channel genes, contractile protein genes, phospholamban encoding genes and genes encoding 1 adrenergic receptors or β adrenergic kinases.

Angiogenic factors include, but are not limited to FGF-1, FGF-2, FGF-5, VEGF, HIF-1 and the like. Proteins useful for treating restenosis include thymidine kinase, cytosine deaminase, p21, p27, p53, Rb, and NF-kB. Hence, this invention can be used to deliver any protein via an rAAV vector that has a therapeutic benefit for treating or ameliorating a cardiovascular condition or disease.

A protein competent to induce angiogenesis or an "angiogenesis factor" as used herein is a protein or substance that causes proliferation of new blood vessels and includes fibroblast growth factors, endothelial cell growth factors or other proteins with such biological activity. Particular proteins known to induce angiogenesis are FGF-1, FGF-2, FGF-5, VEGF and active fragment thereof, and HIF-1. Proteins competent to inhibit angiogenesis or "anti-angiogenesis factors" are proteins or substances that inhibit the formation of new blood vessels.

Anti-sense RNA that can be administered to treat or ameliorate cardiovascular conditions have one of the same activities as proteins useful in the invention. Such RNA include, but are not limited to, c-myb, c-myc and others. Anti-sense RNA molecules, including how to design and use such molecules in expression vectors are well know in the art and can be contructed by routine methodology. Thus a strand of RNA whose sequence of bases is complementary to the sense, or translated, RNA strand can form a duplex to block translation or degradation of a particular mRNA or otherwise control or alter expression of the desired mRNA.

As used herein, a "control region" or "regulatory element" refers to polyadenylation signals, upstream regulatory domains, promoters, enhancers, transcription termination sequences and the like which regulate the transcription and translation of a nucleic acid sequence.

The term "operably linked" refers to an arrangement of elements wherein the components are arranged so as to perform their usual function. Thus, control regions or regulatory elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The regulatory elements of the invention can be derived from any source, e.g., viruses, mammals, insects or even synthetic, provided that they function in cardiomyocytes. For example, any promoter can used to control expression of the transgene. Such promoters can be promiscous, i.e., active in many cell types, such as the SV40 early promoter, the mouse mammary tumor virus LTR promoter, the adenovirus major late promoter (Ad MLP), a herpes simplex promoter, a CMV promoter such as the CMV immediate early promoter, a rous sarcoma virus (RSV) promoter. Alternatively the promoter can be tissue-specific for expression in cardiomyocytes.

The rAAV is delivered to cardiac myocytes by infusion into a coronary artery or coronary sinus. This mode of delivery has also been referred to as intraluminal delivery through a coronary artery, intracoronary delivery or intraarterial delivery. As used herein, infusion into a coronary artery includes intracoronary perfusion. In accordance with the invention, the rAAV vector can be infused when the heart is in situ, i.e., in the body cavity or when the heart or heart tissue (cardiac tissue) has been removed from the body as might occur when the heart is being donated for transplant into a recipient. In the case of a heart being prepared for transplantation or for heart tissue, the vector can be infused through any artery or vein attached thereto, by contacting with or soaking the heart in an appropriately concentrated solution of the vector, or by a combination of both. Thus as described herein, infusion includes delivering rAAV to a heart or heart tissue ex vivo by the means disclosed herein. If necessary, the infusion can be repeated at intervals such as 3 months, 6 months, one year, or as appropriately determined.

As used herein, treating cardiac conditions include treating cardiac or cardiovascular diseases. Examples of cardiac conditions subject to treatment or amelioration according to the method of the present invention include, but are not limited to, myocardial ischemia, myocardial infarction, congestive heart failure, dilated and hypertrophic cardiomyopathy, cardiac arrythmia, cardiac hypertrophy, cardiac transplantation and rejection. For example, if the cardiac condition, such as ischemia, can be treated or improved by inducing angiogenesis, then the rAAV vector used in accordance with the method of this invention would encode an angiogenesis factor.

Thus the rAAV vector is infused into a coronary artery for a time and in an amount sufficient to stably and efficiently transduce cardiac tissue perfused by the artery, wherein the AAV vector encodes a therapeutically-effective molecule which is expressed in the cardiac tissue in an amount effective to treat or ameliorate a cardiovascular condition including, but not limited to, inducing angiogenesis, inhibiting angiogenesis, stimulating or inhibiting cell proliferation, treating restenosis, treating atherosclerosis, treating congestive heart failure, treating ischemic cardiomyopathies or treating malignant arrhythmias, myocardial infarction, congestive heart failure, or dilated and hypertrophic cardiomyopathy.

The method of the present invention can be used with any animal, including but not limited to, mammals such as rodents, dogs, cats, cattle, primates and humans. Preferably the method is used for gene therapy to treat human acquired or inherited cardiac conditions or diseases.

The present invention thus provides a method of treating and/or ameliorating a cardiovascular condition by infusing an rAAV vector for a time and in and amount sufficient to stable and efficiently transduce cardiomyocytes which was heretofore unachievable by methods known in the art. For this invention, stable and efficient transduction means that significant number of cardiomyocytes are transduced and are capable of expressing the protein for a prolonged period of time. Stable and efficient transduction occurs over a period of time and can actually be observed over time as an increase in the percentage of transduced cardiomyocytes, as continued expression of the transgene, or as continued observation of the therapeutic effect at a molecular, microscopic or macroscopic level. For example, with angiogenesis, stable and efficient transduction can be manifested by ongoing development and or growth of new blood vessels, by observing the improved blood flow to the heart, or by determining measuring the level of ischemia in the heart tissue.

Alternatively, efficient transduction occurs when at least about 10%, and preferably more, of the cardiomyocytes have been transduced, i.e., infected by, the rAAV. By following the methods of the invention and by observing at particular times after transduction ranging over a few to many weeks, about 25%, about 40% or even about 50% of the cardiomyocytes will be transduced. While about 10% of the cardiomyocytes can be transduced using only rAAV, this percentage can be increased by co-infusing adenovirus as a helper virus without adverse effects.

The time of infusion contributes to acheiving stable and efficient transduction of the cardiomyocytes as well. Thus the infusion time ranges from about 2 minutes to about 30 minutes, more preferably from about 5 minutes to about 20 minutes and most perferably is about fifteen minutes.

The amount of rAAV infused into the animal is proportional to the body weight of the animal. Hence in accordance with the invention, stable and efficient transduction occurs when the amount of rAAV infused ranges from about $1 \times 10^5$ IU (infectious units) of AAV per gram body weight to about $1 \times 10^9$ IU AAV per gram body weight, and preferably from about $1 \times 10^6$ IU AAV per gram body weight to about $1 \times 10^8$ IU AAV per gram body weight, and most preferably is about $5-6 \times 10^7$ IU AAV per gram body weight.

The example described below demonstrates efficient and stable transduction of cardiac myocytes in vivo after intracoronary infusion of an rAAV vector.

Throughout this application, various publications, patents, and patent applications have been referred to. The teachings and disclosures of these publications, patents, and patent applications in their entireties are hereby incorporated by reference into this application to more fully describe the state of the art to which the present invention pertains.

It is to be understood and expected that variations in the principles of invention herein disclosed in an exemplary embodiment may be made by one skilled in the art and it is intended that such modifications, changes, and substitutions are to be included within the scope of the present invention.

EXAMPLE

Intracoronary Infusion of rAAV

I. Methods

Plasmids and Viruses

The structure of pAAV$_{CMV-LacZ}$ is shown in FIG. 1. Ad$_{CMV-LacZ}$ and the E3-deleted adenovirus, Ad$_{d1309}$, were propagated and purified as described (Barr 1994).

Propagation and Purification of rAAV rAAV was prepared as described (Rolling et al. (1995) *Mol. Biotechnol.* 3:9–15) and purified by cesium chloride gradient centrifugation. Viral titer was assessed by a dot blot hybridization assay to determine the number of viral genomes per milliliter and by infecting HeLa cells with the virus and staining with X-gal 24 hours after infection. All viral preparations had titers of 1 to $2 \times 10^{11}$ genomes/mL, and 2 to $3 \times 10^9$ infectious units (IU)/mL.

Intracoronary Perfusion with rAAV

Adult C57BL/6 mouse hearts were perfused via the left carotid artery with cardioplegia solution (110 mmol/L NaCl, 25 mmol/L KCl, 22 mmol/L NaHCO$_3$, 16 mmol/L MgCl$_2$, 0.8 mmol/L CaCl$_2$, 40 mmol/L glucose) at 4° C. until they stopped beating. They were then perfused ex vivo for 15 minutes with $1.5 \times 10^9$ IU of AAV$_{CMV-LacZ}$ in 0.5 mL of PBS at a rate of 33 μL/min at 4° C. After perfusion, the hearts were transplanted into the neck of a syngeneic host with anastomosis of the donor aorta to the right common carotid artery of the host and anastomosis of the donor pulmonary artery to the right external jugular vein (Lin et al. (1990b) *J. Heart Transplant.* 9:720–723) (n=3 for each time point).

X-Gal Staining

Freshly isolated hearts were fixed in PBS plus 1.25% glutaraldehyde for 10 minutes at room temperature, stained overnight with X-gal (Lin 1990a), and counterstained with eosin.

β-Galactosidase Activity

Cardiac homogenates were assayed for β-galactosidase (β-gal) activity and protein concentrations. β-Gal activities were normalized for total protein and for the number of infectious rAAV or RDAd particles injected.

II. Results

Figure 2:
FIG. 2. Gene transfer into cardiomyocytes in vivo with $AAV_{cMV\text{-}LacZ}$. Gross sections (left) and photomicrographs (right) of mouse hearts after coronary artery perfusion with $1.5 \times 10^9$ IU of $AAV_{cMV\text{-}LacZ}$ and staining with X-gal. Bar=25 microns.
Figure 2:
Figure 2:
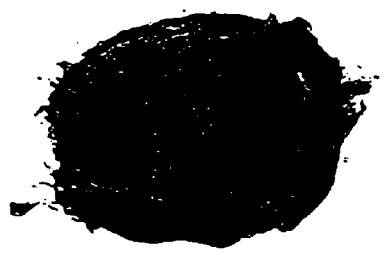
Figure 2:
Figure 2:
Figure 2:
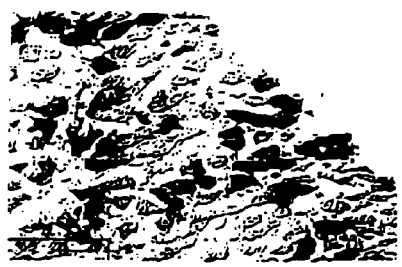

Many clinical applications of myocardial gene therapy may require the stable and efficient transduction of cardiomyocytes distributed throughout large areas of myocardium. Coronary artery infusions of RDAd have been shown to result in the efficient transduction of cardiomyocytes throughout the region of perfused myocardium (Barr 1994). To test whether rAAV is similarly capable of transducing cardiomyocytes after coronary artery perfusion, hearts from C57BL/6 mice were explanted and perfused with $1.5 \times 10^9$ IU of AAV$_{CMV-LacZ}$ for 15 minutes at 4° C. via a catheter placed in the left common carotid artery. These perfused hearts were then transplanted into syngeneic hosts, and the arterial circulation was reestablished by anastomosis of the transplanted aorta to the recipient carotid artery. Such transplanted and revascularized hearts resumed beating and continued to do so until the recipient mice were killed 2, 4, or 8 weeks after perfusion. Two weeks after perfusion, small numbers (<1%) of β-gal-positive cardiomyocytes were detected throughout the myocardium of the rAAV-perfused hearts (FIG. 2). By 4 weeks after perfusion, ≈40% of the cardiomyocytes were β-gal positive. This high level of transduction was stable at weeks after perfusion, with >50% of the cardiomyocytes continuing to express β-gal. Similar increases in recombinant gene expression over the first several weeks after rAAV infection have been observed in skeletal muscle (Fisher 1997; Kessler 1998). It has been postulated that such increases may reflect the gradual process of conversion of the single-stranded AAV genome into a double-stranded DNA molecule that is competent for transcription of the transgene (Ferrari et al. (1996) *J. Virol.* 70:3227–3234). Thus, rAAV delivered by coronary artery perfusion can be used to stably transduce cardiomyocytes throughout the myocardium.

What is claimed is:

1. A method for stable and efficient transformation of cardiomyocytes which comprises:
    infusing a recombinant adeno-associated virus (AAV) vector into a coronary artery or a coronary sinus of an animal in an amount of about $1 \times 10^5$ to about $1 \times 10^9$ infectious units (IU) AAV per gram body weight and for a time sufficient to stably and efficiently transduce cardiomyocytes perfused through said artery or said sinus, wherein said AAV vector comprises at least one nucleic acid molecule operably linked to a control region, said nucleic acid molecule encoding an angiogenic protein, wherein at least 10% of the cardiomyocytes are transduced with the AAV and the AAV is present in the transduced cardiomyocytes for at least 4 weeks.

2. The method of claim 1, wherein said AAV transduces at least about 40% of said cardiomyocytes.

3. The method of claim 1, wherein said AAV is infused for at least about 2 minutes to about 30 minutes.

4. The method of claim 3, wherein about $1 \times 10^6$ IU AAV per gram body weight to about $1 \times 10^8$ IU AAV per gram body weight is infused.

5. The method of claim 4, wherein about $6 \times 10^7$ IU AAV per gram body weight is infused.

6. The method of any one of claims 3, 4, or 5, wherein said AAV is infused for about 5 to about 20 minutes.

7. The method of claim 6, wherein said AAV is infused for about 15 minutes.

8. The method of claim 1, wherein said AAV is infused for at least about 5 minutes to about 20 minutes.

9. The method of claim 1, wherein said AAV is infused for about 15 minutes.

10. The method of claim 1, wherein said amount of AAV is about $1 \times 10^6$ IU AAV per gram body weight to about $1 \times 10^8$ IU AAV per gram body weight.

11. The method of claim 10, wherein said amount of AAV is about $6 \times 10^7$ IU AAV per gram body weight.

12. The method of claim 1, wherein about $6 \times 10^7$ IU AAV per gram body weight is infused for about 15 minutes.

13. The method of claim 1, wherein said coronary artery is infused ex vivo or in vivo.

14. The method of claim 1, wherein said angiogenic protein is FGF-1, FGF-2, FGF-5, VEGF, or HIF-1.

15. The method of claim 1, wherein said cardiomyocytes are in an individual having a vascular condition selected from the group consisting of restenosis, atherosclerosis, congestive heart failure, ischemic cardiomyopathy, malignant arrhythmia, myocardial infarction, congestive heart failure, and dilated and hypertrophic cardiomyopathy.

* * * * *